United States Patent

Hirano et al.

[11] Patent Number: 5,532,015
[45] Date of Patent: Jul. 2, 1996

[54] PROCESS FOR PRODUCING α-L-ASPARTYL-L-PHENYLALANINE METHYL ESTER

[75] Inventors: Atsuhiko Hirano, Kawasaki; Satoshi Yamahara, Yokkaichi; Takehiko Kataoka; Shinichi Kishimoto, both of Kawasaki, all of Japan

[73] Assignee: Ajinomoto Co., Inc., Tokyo, Japan

[21] Appl. No.: 345,469

[22] Filed: Nov. 21, 1994

[30] Foreign Application Priority Data

Nov. 19, 1993 [JP] Japan .................................. 5-290453

[51] Int. Cl.⁶ ......................... A23L 1/236; C07C 229/24
[52] U.S. Cl. .................................. 426/548; 560/41
[58] Field of Search ......................... 560/41; 426/548

[56] References Cited

FOREIGN PATENT DOCUMENTS 0256515  2/1988  European Pat. Off. ..
0255092  2/1988  European Pat. Off. ..

Primary Examiner—José G. Dees
Assistant Examiner—Joseph M. Conrad, III
Attorney, Agent, or Firm—Oblon, Spivak, McClelland, Maier & Neustadt

[57] ABSTRACT

A process for quickly and reproducibly obtaining α-L-aspartyl-L-phenylalanine methyl ester with controlled water content is disclosed. Wet crystals of α-L-aspartyl-L-phenylalanine methyl ester obtained by crystallization are subjected to a drying step to adjust the water content to not more than 5 wt %, and subsequently a gas adjusted to a temperature of 20–80° C. and relative humidity of 20–90 RH % is contacted with the dried crystals to control water content.

10 Claims, No Drawings

PROCESS FOR PRODUCING α-L-ASPARTYL-L-PHENYLALANINE METHYL ESTER

BACKGROUND OF THE INVENTION

1. Field of the Invention

This invention relates to a process for quickly and reproducibly obtaining α-L-aspartyl-L-phenylalanine methyl ester (hereinafter referred to as α-APM) having a controlled water content.

2. Discussion of the Background

α-APM is used as a low calorie dietary sweetener which is about 200 times as sweet as sugar. The final product of α-APM is generally produced in the form of dried powder or granules. Processes for producing granules include a method wherein wet extrusion granulation is carried out before drying (Japanese Patent Application Laid-open No. 95862-1984) and a method wherein dry compression granulation is carried out after drying (Japanese Patent Publication No. 15268-1989). Various means for drying, such as flush drying, fluidized drying, and drying under reduced pressure may be employed.

The water content of α-APM after drying is desirably not more than 5 wt %, based on the weight of wet material, to minimize adhesion of material to the apparatus or walls of the pipe during subsequent transporting and packaging steps. However, the particular value of water content may vary considerably depending on the means and conditions of drying. Drying steps conducted under the same drying conditions often provide dried products with different water contents. For example, when the wet crystal cake obtained by crystallization is crushed and subjected to fluidized drying, it is inevitable that the wet crystal cake is unevenly crushed and unevenly dried depending on the unevenness of crushing, providing a variation of water content of about 1–2% in the final dried product. To avoid such problems, multi-step crushing and grinding of crystals may be conducted as the drying degree proceeds, so that the crystals are uniformly dried to have a water content around the desired value. However, determining the correct conditions and conducting such multi-step operations are often very complicated.

Moreover, the water content of the dried product is known to vary considerably depending on the heat load, i.e., the amount of wet crystals to be dried. For example, we found that under certain conditions wet crystals of α-APM with a water content of 25% could be continuously flush dried using hot air at 170° C. to produce material having 3.5% water. However, if the amount of supplied wet crystals was reduced to half for convenience during the preceding step, the water content of the dried product was significantly reduced, i.e., from about 3.5 to about 1.6%.

Such variations become a problem particularly when the acceptable water content of the final dried product is fixed within a limited range. For example, in the above flush drying process, the dried product having only 1.6% water content would have to be redissolved, and again subjected to the steps from recrystallizing to drying, if the standard water content is restricted to 3–4%. Such problems mean that operations beyond those which are strictly essential for production must be performed and equipment availability is reduced, which are two of the main reasons for increased cost of production. To avoid these variations in water content the drying conditions, including the amount and temperature of hot air, should be changed in accordance with the load. However, it requires much labor to determine the correct drying conditions.

When the acceptable water content in the dried product is fixed to a defined value or lower, manufactures earnestly try not to produce products which are above the standard. In practice, that means that they frequently employ too much drying strength during the drying step. As a result, overdried products with relatively low and uneven water content are often obtained. Considering the stability of the crystals and DKP production during storage of the dried product, in addition to adhesion of the dried product in the steps after drying, water content of the dried α-APM is desirably within the range of 2.5–4%. It is not desirable to evenly obtain overdried product with relatively low water content. Further, α-APM tends to produce IIB-type crystals with poor solubility upon overdrying. Accordingly, to avoid losses due to production of products below the standard water content, and to further enhance ease of handling and storage stability as well as solubility of the dried product, it is important to control the water content of the dried α-APM to a fixed value.

SUMMARY OF THE INVENTION

An object of the invention is to develop a process for reproducibly obtaining α-APM with controlled water content which comprises: drying wet crystals of α-APM obtained upon crystallization to adjust the water content to not more than 5 wt % on a wet basis, followed by contacting α-APM with a gas adjusted to a temperature of 20°–80° C. and relative humidity of 20–90 RH % to control water content.

DETAILED DESCRIPTION OF THE PREFERRED EMBODIMENTS

The present inventors have studied intensively to solve the above problems. As a result, we have obtained a surprising finding, that is, α-APM with controlled water content can be stably produced by first drying wet crystals of α-APM obtained by crystallization, then contacting the product obtained by such a drying step with an air flow at a fixed temperature and humidity. That is, if we know the temperature and humidity of the environment under which equilibrium water content of the particular crystal form agrees with the objective water content, even dried product with widely ranging water content can be converted in a short time to a humidity-adjusted product having the desirable water content, by passing a gas adjusted at said temperature and said humidity. Humidity-adjusted products obtained in this way, when stored in an environment in which the equilibrium humidity is different from the water content of said product, can retain their water content for a long period of time if they are appropriately packaged.

The present inventors have succeeded in solving the above problems and stabilizing steps by applying such findings to a practical process for producing α-APM. That is, the present invention is a process for producing α-L-aspartyl-L-phenylalanine methyl ester which is characterized by drying wet crystals of α-L-aspartyl-L-phenylalanine methyl ester obtained by crystallization to adjust water content to not more than 5 wt % (wet basis), and contacting it with an air flow adjusted to a temperature and relative humidity of 20°–80° C. and 20–90 RH %, respectively, to control water content.

The crystal forms of α-APM after drying include, for example, I type and II type (Japanese Patent Application Laid-open No. 172444-1984). The equilibrium water content to the temperature and humidity of the environment vary depending, for example, on the particular crystal form. Accordingly, it is impossible to fix the temperature and humidity of the air to be contacted with the dried α-APM to a specified value. However, lower temperature and lower humidity require longer contacting time because changes in water content of the contacted α-APM crystals are slower. Higher temperature and higher humidity are accompanied with considerable generation of DKP during the contact, which cannot be disregarded, and results in product quality problems. Desirably, the temperature and humidity is within the range of 20°–80° C. and 20–90 RH %, more desirably within the range of 30°–60° C. and 30–90 RH %, respectively. Using a gas adjusted within the above ranges, the water content of the dried product of α-APM can be controlled to the desired value within a short time, i.e., in an hour. Further, if α-APM after drying contains IIB type crystals, they can be readily converted to IIA type crystals during control of water content. Accordingly, the above problem of solubility can be solved.

As the gas to be contacted with the dried α-APM, air is advantageously used considering cost. An inert gas or a mixture of air and inert gas may be used. The term inert gas as used herein means a gas with low reactivity with α-APM within the above temperature and humidity ranges. Examples include nitrogen, carbon dioxide, helium and argon.

The forms of the dried product to be contacted with the gas with which temperature and humidity are adjusted include powder, granules, crushed cake and the like. To attain uniform contact with gas, it is desirably in the form of powder or granules.

As the contacting device, conventional solid-gas contacting devices, such as fluidized bed devices and flush devices can be used. In particular, fluidized bed devices which have a high contact efficiency of α-APM crystals and a gas can be used to shorten the contacting time required to obtain the desired water content, thus minimizing equipment cost for treating a specified amount of α-APM. The operation may be either a continuous or a batch process. The average contacting time of the dried α-APM and the gas corresponds to the average residence time in a continuous process and the draft time in a batch process. When a fluidize bed device is used, the required value of gas flow varies depending on the form and amount of the dried product to be charged. It is not necessarily more than the minimal fluidizing speed. It is suitably in the range from 0.1 to 4 m/sec (as a linear velocity) for a charged amount of 10–200 kg/m$^2$ per unit fluidized bed.

According to the present process, even when the water content of α-APM immediately after drying varies, humidity-adjusted product with a fixed water content can be stably obtained by an industrial scale operation. As a result, complicated examination to determine drying conditions can be eliminated, and, further, dried products below the specified standard do not have to be redissolved and recycled to the main step, resulting in fewer operations and enhanced availability of equipment. Accordingly, this process is valuable because the steps are rationalized.

Other features of the invention will become apparent in the course of the following descriptions of exemplary embodiments which are given for illustration of the invention and are not intended to be limiting thereof.

EXAMPLE 1

Wet crystals obtained by crystallization of α-APM were subjected to fluidized drying at 60° C. to obtain 2 types of α-APM powders having different water content ((A) 2.6% and (B) 3.5%). The crystal forms of (A) and (B) are completely IB. The sample (A) (250 g) was charged in a fluidized bed device (fluidized bed area, 0.0028 m$_2$), and fluidized by passing a gas adjusted to an inlet temperature of 40° C. and relative humidity of 50 RH % at a linear velocity of 0.4 m/sec. Such fluidizing and humidity adjustment operations were carried out for 10 minutes. The same operations were carried out for Sample B. The water content of samples (A) and (B) after treatment, measured by Karl Fischer's method, were in the range of 3.1–3.2%. X-ray powder diffraction measurement showed no changes in crystal form of either sample after humidity adjustment.

EXAMPLE 2

Powders of α-APM mainly containing IB crystals with 10% of IIA (water content: (A) 2.5%; (B) 3.4%,) obtained by flush drying were compressed and granulated. A fluid device with fluidized bed area of 0.5 m$^2$ was used for granulated samples (A) and (B), fluidizing and humidity-adjustment operations were continuously conducted. The operation conditions were as follows: Air inlet temperature, 40° C.; relative humidity, 40 RH %, supplied at a linear velocity of 0.4 m/s; feed of the sample, 180 kg/hr; residence time of the sample in the device, 10 min. Water content of the humidity-adjusted product, measured according to Karl Fischer's method, was within the range of 3.2–3.3%. X-ray powder diffraction measurement showed no change in crystal form.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States:

1. A process for controlling the water content of α-L-aspartyl-L-phenylalanine methyl ester which comprises: drying wet crystals of α-L-aspartyl-L-phenylalanine methyl ester obtained upon crystallization to adjust the water content to not more than 5 wt % on a wet basis, followed by contacting dried α-L-aspartyl-L-phenylalanine methyl ester with a gas adjusted to a temperature of 20°–80° C. and relative humidity of 20–90 RH % to control water content.

2. A process according to claim 1, wherein the inlet temperature and relative humidity of the gas to be contacted with α-L-aspartyl-L-phenylalanine methyl ester are within the range of 30°–60° C. and 30–90 RH %, respectively.

3. A process according to claim 1 wherein a fluidized bed apparatus is employed to contact said dried α-L-aspartyl-L-phenylalanine methyl ester with a gas of which temperature and humidity are adjusted.

4. A process according to claim 3, wherein the amount of α-L-aspartyl-L-phenylalanine methyl ester to be supplied to said fluidized bed apparatus is within the range of 10–200 kg/cm$^2$ unit area of the fluidized bed, and the linear velocity of the gas to be supplied is within the range of 0.1–4.0 m/sec.

5. A process according to any one of claim 1 wherein the average time for contacting dried α-L-aspartyl-L-phenylalanine methyl ester with the temperature- and humidity-adjusted gas is within an hour.

6. A process according to claim 1 wherein the of α-L-aspartyl-L-phenylalanine methyl ester to be contacted with said temperature- and humidity-adjusted gas is in the form of powder or granules.

7. A process according to claim 1 wherein the crystal form of α-L-aspartyl-L-phenylalanine methyl ester to be contacted with temperature- and humidity-adjusted gas is type I or II, or a mixture thereof.

8. A process according to claim 7, wherein the type II crystals of α-L-aspartyl-L-phenylalanine methyl ester contacted with temperature- and humidity-adjusted gas are type IIB or a mixture of IIA and IIB.

9. A process according to claim 1 wherein the gas to be contacted with dried α-L-aspartyl-L-phenylalanine methyl ester is air or an inert gas, or a mixture thereof.

10. A process according to claim 1 wherein the gas to be contacted with dried α-L-aspartyl-L-phenylalanine methyl ester is air.

* * * * *